United States Patent [19]

Adams et al.

[11] Patent Number: 5,334,501
[45] Date of Patent: Aug. 2, 1994

[54] QUANTIFICATION OF BACTERIA USING A NUCLEIC ACID HYBRIDIZATION ASSAY

[75] Inventors: Trevor H. Adams, Woodinville; Dennis E. Schwartz, Redmond; Nicolaas M. J. Vermuelen, Woodinville; Roy H. Kanemoto, Seattle, all of Wash.

[73] Assignee: Microprobe Corporation, Bothell, Wash.

[21] Appl. No.: 41,804

[22] Filed: Apr. 1, 1993

Related U.S. Application Data

[63] Continuation of Ser. No. 631,131, Dec. 19, 1990, abandoned, which is a continuation of Ser. No. 378,355, Jul. 11, 1989, abandoned.

[51] Int. Cl.$^5$ .................. C12Q 1/68; C07H 21/04; C07H 21/02; C12N 15/00
[52] U.S. Cl. .................. 435/6; 536/23.1; 536/24.32; 935/77; 935/78
[58] Field of Search .................. 536/24.32

[56] References Cited

FOREIGN PATENT DOCUMENTS

| 0127327 | 12/1984 | European Pat. Off. |
| WO88/03957 | 2/1988 | PCT Int'l Appl. |
| WO89/06704 | 7/1989 | PCT Int'l Appl. |
| 2169403 | 7/1986 | United Kingdom |
| 8803957 | 6/1988 | World Int. Prop. O. |

OTHER PUBLICATIONS

Hames et al, Nucleic Acid Hybridization, CRL Press, 1985, p. 196.
Matthews et al, Analytical Biochem, v. 169, Feb. 1988, 1-25.
Thompson, J., et al., "Molecular Hybridization with RNA Probes in Concentrated Solutions of Guanidine Thiocyanate," *Anal. Biochem.*, 163:281-291 (1987).
Lane, D. J., "Rapid determination of 16S ribosomal RNA sequences for phylogenic analyses," *Proc. Natl. Acad. Sci. USA* 82:6955-6959 (Oct. 1985).
Shinozaki, K., et al., "The complete nucleotide sequence of the tobaco chloroplast genome: its gene organization and expression," *The EMBO Journal* 5(9):2043-2049 (1986).
Umesono, K., et al., "Nucleotide sequence of *Marchantia polymorpha* chloroplast DNA: a region possibly encoding three tRNAs and three proteins including a homologue of *E. coli* ribosomal protein S14," *Nucleic Acids Research* 12(24):9551-9565 (1984).
J. Thompson and D. Gillespie, *Anal. Biochem.* 163:281-291, 1987.
Gowans, E. J., et al., "Detection of Specific DNA and RNA Sequences in Tissues and Cells by in situ Hybridization," Nucleic Acid Probes, (Chapter 5, 1989) 139-158.
Anderson, M. L. M., et al., "Quantitative Filter Hybridisation" (Chapter 4) in Nucleic Acid Hybridisation a Practical Approach, Eds. B. D. Hames and S. J. Higgins, IRL Press, Washington, D.C. USA.
Giovannoni, S. J., et al., "Phylogenetic Group-Specific Oligodeoxynucleotide Probes for Identification of Single Microbial Cells," *Journal of Bacterioloy*, (Feb. 1988), 720-726.
Chuba, Paul J., "Synthetic Oligodeonucleotide Probes for the Rapid Detection of Bacteria Associated with Human Peridontitis," *Journal of General Microbiology*, (1988), 134:1931-1938.
Woese, C. R., et al., "Conservation of primary structure in 16S ribosomal RNA," *Nature*, (1975) 254:83-85.
Socransky, S. S., et al., "The MicroBiota of the Gingival Crevice Area of Man—I: Total Microscopic and Viable Counts and Counts of Specific Organisms," *Arch. Oral. Biol.*, (1963) 8:275-280.
Moore, W. E. C., "Microbiology of peridontal disease," *J. Peridontal Res.*, 22:335-341.
*J. of Dental Res.*, Annual Session, Mar. 15-19, 1989, vol. 68, p. 197, Abstract Nos. 122-124.

*Primary Examiner*—Mindy B. Fleisher
*Attorney, Agent, or Firm*—Townsend and Townsend Khourie and Crew

[57] ABSTRACT

This invention provides for a method of quantifying bacteria using a bacterial specific nucleic acid probe which is complementary to a unique and highly conserved region of the 16S ribosomal RNA (rRNA) of bacteria. This probe permits the rapid detection of 16S rRNA in a sample and by comparison with known standards, one can estimate the total bacterial count in the sample. The method is accurate and reproducible and conducted at temperatures of between about 120° to about 40° C.

19 Claims, No Drawings

QUANTIFICATION OF BACTERIA USING A NUCLEIC ACID HYBRIDIZATION ASSAY

This is a continuation Ser. No. 07/631,131, filed Dec. 19, 1990, now abandoned which was a continuation of application Ser. No. 07/378,355, filed Jul. 11, 1989, now abandoned.

BACKGROUND OF THE INVENTION

1. Field of the Invention

This invention provides for a method of quantifying bacteria using a bacterial specific nucleic acid probe which is complementary to a unique, open and highly conserved region of the 16S ribosomal RNA (rRNA) of bacteria. This probe permits the rapid detection of 16S rRNA in a sample and by comparison with known standards, one can estimate the total bacterial count in the sample. The method is accurate, reproducible and conducted at room temperature.

2. Information Disclosure

The use of signal intensity of nucleic acid hybridization assay to estimate total nucleic acid present in a sample is known. Gowans, E. J., Jilbert, A. R. and Burrell, C. J., Detection of Specific DNA and RNA Sequences in Tissues and Cells By In Situ Hybridization (Chapter 5, 1989) in Nucleic Acid Probes, Ed. Symons, R. H., CRC Press, Inc. Boca Raton, Fla.; and Anderson, M. L. M. and Young, B. D., 1987, Quantitative Analysis of Solution Hybridization, (Sec. 10) in Nucleic Acid Hybridization a Practical Approach, Eds. B. D. Hames and S. J. Higgins, IRL Press, Washington D.C. U.S.A.

Universal probes for the detection of bacteria are known. Giovannoni, S. J. et al., 1988, Phylogentic Group-specific Oligodeoxynucleotide Probes for Identification of Single Microbial Cells, J. Bact. 170(2):720-726 and Chuba, P. J. et al., 1988, Synthetic Oligodeoxynucleotide Probes for the Rapid Detection of Bacteria Associated with Human Periodontitis, J. Gen. Microbiol. 134:1931-1938. Oligonucleotides reflecting the UP9A region were described by Woese, C. R., et al., (1975), Conservation of primary structure in 16S ribosomal RNA, Nature 254:83-85 (see Table 1, oligos 47, 49 and 51) and WO 88/03957 (see page 105).

The use of total bacterial count to diagnose periodontal disease is not a presently accepted practice. Socranksky, S. S. et al., The Microbiota of the Gingival Crevice Area of Man-I Total Microscopic and Viable Counts and Counts of Specific Organisms, Arch. Oral. Biol 8:275-280 and Moore, W. E. C., 1987, Microbiology of Periodontal , Disease, J. Periodontal Res. 22:335-341.

Microbial counts were used to determine the effectiveness of tetracycline for prevention of periodontal disease by the Forsyth Center and reported in J. of Dental Res. Annual Session, Mar. 15-19, 1989, Vol. 68, page 197, Abstract Nos. 122-124.

SUMMARY OF THE INVENTION

This invention provides for a method of measuring the quantity of bacteria in a biological sample which comprises lysing the bacteria in the sample and contacting the lysate under hybridization conditions with an oligonucleotide probe having a sequence of 5'CTGCTGCCTCCCGTAGGAGT3'. The phrase "an oligonucleotide probe having a sequence of 5'CTGCTGCCTCCCGTAGGAGT3', is meant to include functional equivalents of this sequence. Such equivalents are described in greater detail below but embrace nucleic acid analogs and minor mismatched oligonucleotides, such that the probes will bind specifically to the target region on the 16S rRNA to which the claimed sequence is complementary.

The term "lysate" refers to solutions containing bacterial nucleic acid. A lysate would include crude mixtures of disrupted bacteria, semi-purified solutions and purified solutions of bacterial nucleic acid.

The claimed probe may either be a capture probe or signal probe. Capture probes are unlabelled probes which bind to target nucleotides and subsequently capture the target to a solid support. Signal probes are adapted to be used for the generation of a signal, for example a probe with a avidin moiety.

Samples can be obtained from any biological source including a human being and particularly from blood, mouth region or anogenital region.

The method can be further enhanced by the addition of at least one additional nucleic acid probe which is species specific, genus-specific or strain-specific. These additional probes can provide qualitative information in addition to quantification of bacteria.

This invention also provides for diagnostic kits utilizing the above technology.

DETAILED DESCRIPTION

This invention relates to the use of a unique sequence of nucleic acid, designated UP9A, which provides universal binding to the 16S rRNA (see Table 1). This sequence is particularly unique to bacterial rRNA and does not significantly hybridize to human nucleic acid. In addition this sequence is located in a region of the ribosome where it is available for hybridization with only minimal disturbance of the secondary structure of the rRNA. Thus the quantification assays can be done without heat denaturation of the sample. Target sequences having this characteristic are termed "open" regions because of their relative availability for hybridization.

Quantification of bacteria is dependent upon the ability of the assay to react in a predictable manner to increasing amounts of rRNA. The UP9A probe reacts in predictable manner, typically by offering a direct and linear response to increasing amounts of bacterial rRNA. By preparation of and by comparison to appropriate standards, one can readily quantify the total bacterial count in a sample using the disclosed invention.

It is anticipated that the invention will find application in an unlimited number of clinical and industrial settings where the rapid monitoring of bacterial counts are useful. Bacterial counts are of particular use in diagnosing disease states where high bacterial counts are indicative of the particular disease state. For example bacterial counts are useful in diagnosing periodontal disease, stomach ulcers, bacteremia, and urinary tract infections. In addition, rapid bacterial quantification is often desirable during food preparation and fermentation processes.

TABLE 1

| Examples of Universal Oligonucleotides for 16S bacterial ribosomes. | |
|---|---|
| 16S rRNA oligonucleotide probes | E. coli base position |
| UP7B 5'GTATTACCGCGGCTGCTG3' | 519-536 CITED TO US |
| UP3A 5'TGACGGGCGGTGTGTACAA3' | 1390-1408 |

TABLE 1-continued

Examples of Universal Oligonucleotides for 16S bacterial ribosomes.

| 16S rRNA oligonucleotide probes | E. coli base position |
|---|---|
| UP9A 5'CTGCTGCCTCCCGTAGGAGT3' | 338-357 |

Obtaining Oligonucleotide, UP9A

The degree of complementarity (homology) required for detectable binding of UP9A probes with the rRNA of bacteria will vary in accordance with the stringency of the hybridization medium and/or wash medium. The degree of complementarity will optimally be 100 percent; however, it should be understood that minor variations between the rRNA and UP9A may be compensated for by reducing the stringency of the hybridization and/or wash medium as described below. Thus, despite the lack of 100 percent complementarity under reduced conditions of stringency, functional probes having minor base differences from their rRNA targets are possible. Therefore, under hybridization conditions of reduced stringency, it may be possible to slightly modify the UP9A probe while maintaining an acceptable degree of specificity to quantify total bacteria present.

The UP9A oligonucleotide may be a compound of RNA or DNA. In addition, analogs of nucleosides may be substituted for naturally occurring nucleosides. The advantage of analogs would include greater stability, resistance to nuclease activity and ease of signal attachment. The term UP9A is intended to embrace all functionally equivalent species. Equivalent UP9A probes may also consist of the given sequence, concatemers of the sequence, or probes flanked by about 10 or less bases of any degree of complementarity to the native sequences flanking the UP9A complementary region of bacterial rRNA.

UP9A probe may be chemically synthesized using commercially available methods and equipment. For example, the solid phase phosphoramidite method can be used to produce short probes of between 15 and 50 bases. For this invention, it is preferred to chemically synthesize short DNA probes using the Model 380B DNA Synthesizer from Applied Biosystems, Foster City, Calif., using reagents supplied by the same company.

To obtain large quantities of UP9A probes, one can also clone the desired sequence using traditional cloning methods, such as described in Maniatis, T., et al. Molecular Cloning: A Laboratory Manual, Cold Spring Harbor, N.Y., 1982, or one can produce the probes by chemical synthesis using commercially available DNA synthesizers. An example of cloning would involve insertion of the cDNA for the ribosomal RNA into a replication vector, such as pBR322, M13, or into a vector containing the SP6 promotor (e.g., generation of single-stranded RNA using SP6 RNA polymerase), and transformation of a bacterial host. The DNA probes can be purified from the host cell by lysis and nucleic acid extraction, treatment with selected restriction enzymes, and further isolation by gel electrophoresis.

The use of polymerase chain reaction technology can also be used to obtain large quantities of the UP9A probe. (See U.S. Pat. No. 4,683,202.)

The UP9A probe can be used as a capture probe in a sandwich-type assay where the bacterial rRNA is the target nucleic acid and a second or other signal probes facilitates detection. Table 1 provides UP7B and UP3A which are useful as additional universal probes for signal detection.

UP9A probes can also serve as signal probes. Signal probes may be labeled by any one of several methods typically used to detect the presence of hybrid polynucleotides. The most common method of detection is the use of autoradiography with $^3H$, $^{125}I$, $^{35}S$, $^{14}C$, or $^{32}P$ labeled probes or the like. The choice of radioactive isotope depends on research preferences due to ease of synthesis, stability and half lives of the selected isotopes. Other labels include ligands which bind to antibodies, labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The choice of label dictates the manner in which the label is bound to the probe. Radioactive probes are typically made using commercially available nucleotides containing the desired radioactive isotope. The radioactive nucleotides can be incorporated into probes, for example, by using DNA synthesizers, by nick translation with DNA polymerase I; by tailing radioactive DNA bases to the 3' end of probes with terminal deoxynucleotidyl transferase, by treating single-stranded M13 plasmids having specific inserts with the Klenow fragment of DNA polymerase in the presence of radioactive deoxynucleotides (dNTP), by transcribing from RNA templates using reverse transcriptase in the presence of radioactive deoxynucleotides (dNTP), or by transcribing RNA from vectors containing specific RNA vital promoters (e.g., SP6 promoter) using the corresponding RNA polymerase (e.g., SP6 RNA polymerase) in the presence of radioactive ribonucleotides rNTP.

The probes can be labeled using radioactive nucleotides in which the isotope resides as a part of the nucleotide molecule, or in which the radioactive component is attached to the nucleotide via a terminal hydroxyl group that has been esterified to a radioactive component such as inorganic acids, e.g., $^{32}P$ phosphate or $^{14}C$ organic acids, or esterified to provide a linking group to the label. Base analogs having nucleophilic linking groups, such as primary amino groups, can also be linked to a label.

Non-radioactive probes are often labeled by indirect means. For example, a ligand molecule is covalently bound to the probe. The ligand then binds to an anti-ligand molecule which is either inherently detectable or covalently bound to a detectable signal system, such as an enzyme, a fluorophore, or a chemiluminescent compound. Ligands and anti-ligands may be varied widely. Where a ligand has a natural anti-ligand, namely ligands such as biotin, thyroxine, and cortisol, it can be used in conjunction with its labeled, naturally occurring anti-ligands. Alternatively, any haptenic or antigenic compound can be used in combination with an antibody.

Probes can also be labeled by direct conjugation with a label. For example, cloned. DNA probes have been coupled directly to horseradish peroxidase or alkaline phosphatase, (Renz. M., and Kurz, K. A Colorimetric Method for DNA Hybridization. Nuc. Acids Res. 12:3435-3444, 1984) and synthetic olignucleotides have been coupled directly with alkaline phosphatase (Jablonski, E., et al., Preparation of Oligodeoxynucleotide-alkaline phosphatase Conjugates and Their Use as Hybridization Probes. Nuc. Acids. Res. 14:6115–6128, 1986, and Li P., et al., Enzyme-linked Synthetic Oligonucleotide probes: Non-Radioactive Detection of Enterotoxigenic Escherichia Coli in Faecial Specimens. Nuc. Acids Res. 15:5275–5287 (1987).

Enzymes of interest as labels will primarily be hydrolases, such as phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescers include luciferin, and 2,3-dihydrophthalazinediones, e.g., luminol.

Sample Collection

Microbial specimens for use in this invention can be obtained from any source suspected of harbouring bacteria. The sample collection means should be uniform and reproducible such that meaningful comparisons can be made.

The samples are generally dispersed in a measured amount of buffer, though dispersal may be optimal if lysis is immediately possible. This dispersal buffer generally provides a biologically compatible solution. A typical dispersal buffer solution would be 150 mM NaCl, 20 mM Tris-HCl (pH 7.5), 10 mM EDTA, 10 mM EGTA, or 150 mM NaCl, 20 mM NaPO$_4$ (pH 7.5), 10 mM EDTA, 10 mM EGTA. Samples may be frozen until use.

Prior to quantification, samples suspected of containing bacteria are first subjected to a lysing solution to release cellular nucleic acids. Dispersal of the sample prior to lysis is optional. Lysing buffers are known in the art. EP 199,439; Potts, T. V. and Berry, Em. Internat. J. Sys. Bacter., 33:765–771 (1983); Bonta, Y., et al., J. Dent. Res., 64:793–798 (1985). Generally, these buffers are between pH 7.0 and 8.0, and contain both chelating agents and surfactants. Typically, a lysing solution is a buffered detergent solution having a divalent metal chelator or a buffered chaotrophic salt solution containing a detergent (such as SDS), a reducing agent and a divalent metal chelator (EDTA). The use of enzymes such as N-acetyl-muramidase (lysozyme) or proteases (such as Protease K) will facilitate lysis and offer high quality results.

The sample may be directly immobilized to a support or further processed to extract nucleic acids prior to immobilization. Released or extracted bacterial nucleic acid (including target nucleic acid) are fixed to a solid support, such as cellulose, nylon, nitrocellulose, diazobenzyloxymethyl cellulose, and the like. The immobilized nucleic acid can then be subjected to hybridization conditions.

Alternatively, samples may be collected and dispersed in a lysing solution that also functions as a hybridization solution, such as 3M guanidinium thiocyanate (GuSCN), 50 mM Tris (pH 7.6), 10 mM EDTA, 0.1% sodium dodecylsulfate (SDS), and 1% mercaptoethanol (Maniatis, T. et al. Molecular Cloning: A Laboratory Manual, Cold Spring Harbor, N.Y., 1982).

Hybridization Conditions

Various hybridization solutions may be employed, comprising from about 20 to 60% volume, preferably 30%, of a polar organic solvent. A common hybridization solution employs about 50% v/v formamide, about 0.5 to 1M sodium chloride, about 0.05 to 0.1M buffers, such as sodium citrate, Tris-HCl, PIPES or HEPES (pH range about 6–9), about 0.05 to 0.2% detergent, such as sodium dodecylsulfate, or between 0.5–20 mM EDTA, 0.01–0.05% ficoll (about 300–500 kilodaltons), 0.01–0.05% polyvinylpyrroliodone (about 250–500 kdal), and 0.01–0.05% serum albumin. Also included in the typical hybridization solution will be unlabeled carrier nucleic acids from about 0.1 to 5 mg/ml, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, or polystyrene sulfonic acid and anionic saccharidic polymers, such as dextran sulfate.

An alternative hybridization solution may be employed comprising about 2 to 4M GuSCN, preferably 3M, about 0.01 to 0.1M Tris (pH range about 6.0 to 8.5), a detergent such as sodium dodecyl sulfate in concentrations of about 0.1 to 5% (w/v), and about 0.01 to 0.1M EDTA. Other additives may also be included such as carrier DNA or RNA, or protein such as bovine serum albumin or gelatin. Stringency of the hybridization solution can be adjusted by the addition of about 0 to 10% formamide usually 5%.

The particular hybridization technique is not essential to the invention. Hybridization techniques are generally described in Nucleic Acid Hybridization: A Practical Approach, Ed. Hames, B. D. and Higgins, S. J., IRL Press, 1987; Gall and Pardue (1969), Proc. Natl. Acad. Sci., U.S.A., 63:378–383, and John, Burnstell and Jones (1969) Nature, 223:582–587. As improvements are made in hybridization techniques, they can readily be applied.

The amount of labeled probe which is present in the hybridization solution may vary widely, depending upon the nature of the label, the amount of the labeled probe which can reasonably bind to the cellular target nucleic acid, and the stringency of the hybridization medium and/or wash medium. Generally, substantial excesses of probe over the stoichiometric amount of the target nucleic acid will be employed to enhance the rate of binding of the probe to the target DNA.

Various degrees of stringency of hybridization can be employed. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%.

Assay test protocols for use in this invention are those of convention in the field of nucleic acid hybridization, and include both single phase, where the target and probe polynucleic acids are both in solution, and mixed phase hybridizations, where either the target or probe polynucleotides are fixed to an immobile support. The assay test protocols are varied and are not to be considered a limitation of this invention. A general review of single phase hybridization can be had from a reading of Nucleic Acid Hybridization: A Practical Approach, Ed. Hames, B. D. and Higgins, S. J., IRL Press, 1985, and Hybridization of Nucleic Acids Immobilized on Solid Supports, Meinkoth, J. and Wah, G., Analytical Biochemistry, pp. 238, 267-284, 1984. Mixed phase hybridizations are preferred.

Nucleic acids from GuSCN-lysed bacteria can be immobilized directly on to nitrocellulose or Nytran, and hybridized with the appropriate probe. The GuSCN-lysate is diluted with buffer containing formaldehyde, slotted to nitrocellulose and heated at 80° C. to denature the nucleic acids.

Regardless of the assay test protocol being used, the bacterial cells are to remain in contact with a hybridization solution at a moderate temperature for an extended period of time. In single phase assays, the double-stranded duplexes may be separated from single-stranded nucleic acid by $S_1$ nuclease digestion followed by precipitation of duplex molecules, or by selective binding to hydroxyapatite. In mixed phase assays, the support-immobilized nucleic acids is introduced into a wash solution having analogous concentrations of sodium chloride, buffers, and detergent, as provided in the hybridization solution. The time period for which the support is maintained in the wash solution may vary from several minutes to three hours or more.

Either the hybridization or the wash medium can be stringent. Typically, for mixed phase assays, it is the wash solution that most often determines the stringency and facilitates dissociation of mismatched duplexes. After rinsing the support at room temperature with a dilute buffered sodium chloride solution, the support may now be assayed for the presence of duplexes in accordance with the nature of the label.

Where the label is radioactive, the presence of probe can be detected in a scintillation counter. More conveniently, in mixed phase assays, the substrate can be dried and exposed to X-ray film in any number of conventional autoradiographic protocols.

Where the label is fluorescent, the sample is detected by first irradiating it with light of a particular wavelength. The sample absorbs this light and then emits light of a different wavelength which is picked up by a detector (*Physical Biochemistry*, Freiraider, D., W. H. Freeman & Co., pp. 537-542, 1982).

Where the label is a hapten or antigen, the sample can be detected by using antibodies. In these systems, a signal is generated by attaching fluorescent or enzyme molecules to the antibodies; in some cases the antibody is labeled with a radioactive probe. (Tijssen, P., *Practice and Theory of Enzyme Immunoassay*, Laboratory Techniques in Biochemistry and Molecular Biology, Burdon, R. H., van Knippenberg, Ph.H., Eds., Elsevier, pp. 9-20, 1985.)

One method of detection is enzymatic detection in conjunction with biotin. Although fluorescence is an alternative label, enzymatic labels, in combination with avidin or streptavidin such as biotinylated peroxidase or alkaline phosphatase, are preferred. Enzyme-conjugated avidin or streptavidin can also be used to directly bind the enzyme to the probe (Haase, et al., supra). Preferred enzymes are peroxidase or alkaline phosphatase. An especially preferred method utilizes enzymes directly conjugated to probes. The preferred enzymes are alkaline phosphatase and peroxidase. Methods for conjugating enzymes to oligonucleotides are known. Nucleic Acid Res., 14:6115-6128 (1986) and Nucl. Acid Res., 15:5275-5287 (1987).

In the preferred instance, the UP9A assay protocol is a sandwich-type assay. A primary component of a sandwich-type assay is a solid support. The solid support has adsorbed to it or covalently coupled to it immobilized nucleic acid probe that is unlabeled and complementary to one portion of the rRNA sequence. Preferred are those probes that hybridize to regions of the ribosomal RNA with minimal secondary and tertiary interactions, such as those listed in Table 1. The advantage of such probes is that the hybridization can be carried out without the additional step of heat denaturing the sample nucleic acid. The test sample suspected of containing bacteria is then contacted with the solid support in a hybridization medium. Finally, a second soluble-labeled probe complementary to a different sequence of the rRNA of the pathogenic bacteria is hybridized to the rRNA that has formed a hybridization duplex with the immobilized nucleic acid probe on the solid support. As previously stated, the UP9A probe may function as either a capture or signal probe.

Alternatively, the assay format may be a mixed phase, non-sandwich type assay. In the preferred mode, the entire assay takes place at room temperature. The bacterial sample is lysed in the lysis/hybridization solution which contains one Nytran capture filter and biotinylated signal oligonucleotides. The hybridization is complete in 40 minutes with vigorous shaking (optional). The filter is washed free of hybridization solution and allowed to bind with streptavidin-HRP for 5 minutes with vigorous shaking. The filter is again washed, then placed in development solution for 10 minutes with gentle shaking. Color development is stopped by a final wash and the filter evaluated.

It is also feasible to combine the universal UP9A probe with genus species or strain specific oligonucleotide probes to provide assays capable of quantifying the amount of specific species of bacteria rather than total bacterial count.

Standards

The proportion of UP9A bound to a matrix of bacterial rRNA will increase predictably and reproducibly with the amount of bacterial rRNA in the matrix. To accurately quantify the amount of rRNA present in a sample, one has to prepare standards for comparison. Virtually any label or detection means of use in nucleic acid hybridizations can be standardized and quantified for use with the UP9A probe.

The standards are prepared by taking known quantities of bacteria harboring the UP9A complementary sequence and using such bacteria as a control to compare the intensity of the hybridization signal to the unknown samples. The quantity of signal must correlate with the amount of hybridization such that comparison between the standard and unknowns is possible. For example, the intensity of an autoradiogram can be used to compare relative amounts of hybridization. Typically, a densitometer is used for comparisons. The use of an enzyme-linked probe in a colorimetric assay format would permit the use of automated systems to measure the quantity of bacteria. This is analogous to an ELISA procedure where a spectrophotometer is used to determine the quantity of antigen present in an unknown sample.

Kits

Using the UP9A probe, one can construct commercially diagnostic kits for clinical laboratories. Such kits would include instruction cards and vials containing the various solutions necessary to conduct a nucleic acid hybridization assay. These solutions would include lysing solutions, hybridization solutions, combination lysing and hybridization solutions, and wash solutions. The kits would also include labelled probes. The UP9A probe could be either unlabelled or labelled depending on the assay format. Standard references for comparison of results would also be necessary to provide an easy estimate of bacterial numbers in a given solution. Depending upon the label used additional components may be needed for the kit, e.g. enzyme labels require substrates.

Diagnosing Periodontal Disease by Total Bacterial Count

Using standard culturing procedures the following parameters were developed which permit the diagnosis of periodontal disease using total bacterial count. Total bacterial count is sometimes referred to as "bacterial load."

In a previous and unrelated study by the Forsyth Dental Center, it was reported that pockets of healthy/-plaque-free or post treatment patients contain between $1 \times 10^2$ to $1 \times 10^5$ bacterial cells. Since we could not find any evidence in the literature that anyone has ever suggested that a test for total bacterial load could be useful for the diagnosis of periodontal disease, it was decided to determine the total bacterial load as well as individual pathogenic periodontal bacteria in normal, diseased-, diseased-after treatment with tetracycline fibers and diseased-patients after scraping of the teeth by cultural procedures. Appropriate plaque samples were collected by curette and deposited in culture media and the cell numbers for total bacteria and for the individual pathogenic bacteria were determined by established microbiological techniques as shown in Table 2.

TABLE 2

Average number of total and individual bacterial numbers determined by culture for diseased pockets at the Forsyth Dental Center and the University of Washington.

|  | FORSYTH STUDY[a] | U.W. STUDY[b] |
|---|---|---|
| Total bacteria | $6 \times 10^7$ | $7 \times 10^7$ |
| Individual bacteria | | |
| *Actinobacillus actinomycetemcomitans* (Aa) | $2 \times 10^6$ | $5 \times 10^6$ |
| *Bacteriodes gingivalis* (Bg) | $4 \times 10^6$ | $7 \times 10^6$ |
| *Bacteriodes intermedius* (Bi) | $6 \times 10^6$ | $8 \times 10^6$ |
| *Eikenella corrodens* (Ec) | $3 \times 10^6$ | $4 \times 10^6$ |
| *Fusobacterium nucleatum* (Fn) | $5 \times 10^5$ | $2 \times 10^5$ |
| *Wolinella recta* (Wr) | $1 \times 10^6$ | $3 \times 10^4$ |

[a]100 pockets
[b]76 pockets

TABLE 3

Total bacterial numbers determined by culture for diseased, treated and normal pockets at the Forsyth Center and the University of Washington.

| Disease State | Total bacterial numbers |
|---|---|
| Disease (100)[a] | $6 \times 10^7$ |
| Severe/moderate[b] | $7 \times 10^7$ |
| Post treatment (40)[a] | $2.5 \times 10^6$ |
| Normal (20)[b] | $5 \times 10^6$ |

[a]Determined at the Forsyth Center.
[b]Determined at the U.W.

The following conclusions can be made from the data in Tables 2 and 3:

a) That there is about a 90% drop in the average cell numbers going from the diseased to the normal state.

b) A similar drop in cell numbers is observed when the diseased states are treated with either tetracycline or after scaling.

c) It appears from these two studies that when plaque samples are collected with a curette the diseased state starts when total bacterial cell numbers increase substantially over $5 \times 10^6$ cells.

As more data is accumulated these values will be refined. It should be pointed out that about 10 fold more plaque sample is collected with a curette scrape then with a paper point. Therefore the cutoff cell number for the determination of disease state will depend on the sample collection procedure.

Accumulated evidence exists which confirms a correlation between total bacterial numbers and the state of bacterial vaginosis. Therefore it is possible to determine the total bacterial numbers in the same way as for periodontal disease.

It is known that the progression of bacteremia depends on the total bacterial cell counts. Similarly the total bacterial cell numbers could be determined in the same way as for periodontal disease.

It is observed with peptic ulcers that the pH of the stomach increases and favors the increased growth of bacteria. We therefore believe that the total bacteria number may be indicative of the presence of ulcers. The total bacterial test may therefor also be used in this case.

EXAMPLE 1

Detection of Total Bacteria in Heated GuSCN Lysate Using a Colorimetric Sandwich Assay Format and UP9A-Nytran as a Capture System A lysis solution composed of 3M GuSCN, 2% Sarkosyl, 50 mM Tris, pH 7.6, 25 mM EDTA was used to lyse a mixture of $1 \times 10^8$ cells of Aa, Bg, Bi, Ec, Fn and Wr in 100 microliter volumes at 19° C. The lysate was then heated in a 65° water bath for 10 minutes. Biotinylated 24-mer oligonucleotide probes (UP7B and UP3A) complementary to conserved regions of bacterial 16s rRNA (signal probes) were added to a final concentration of 100 nanograms per ml to both the lysate and to the 3M GuSCN lysing solution that was to be used as the diluent. Seven, ten-fold serial dilutions were then made with the heated lysate and then this solution was incubated with nytran discs which had covalently immobilized 1 microgram of UP9A specific oligonucleotide probe (capture probe) for 1 hour at ambient temperature. The solid supports were then washed with SDS/FW (0.01-2.0% sodium dodecyl sulfate and a filter wash (FW) of 0.09 m NaCl, 0.01 m TRis-HC at pH 7.6 and 5 mM EDTA) at ambient temperature and then incubated with 10 ng/ml of Strepavidin/Horseradish peroxidase (SA/HRP) conjugate in SDS/FW for 30 minutes at ambient temperature. The solid supports were then washed with SDS/FW, FW, and then the presence of peroxidase was determined by incubating the filter with 3 mM 4-methoxynaphthol in 0.1 m citrate buffer, pH 5.5 for 15 minutes. The results indicated that a level of sensitivity of $1 \times 10^6$ bacterial cells was achieved using the heated GuSCN lysate.

EXAMPLE 2

The Quantification of Bacterial Numbers in Plaque Samples

Twenty normal periodontal samples were collected and 1/20th of these samples was taken for microbiological cultural analysis. The nucleic acid from the remaining sample was immobilized on Nytran membrane and then probed with universal primer UP9A. Table 4 illustrates a comparison of the cell numbers determined by micro-culture and by probe analysis. As explained in the experimental section below the number of bacteria can be estimated in the samples by comparing the signal strength of unknowns with that of the standards. It has previously been shown on Nytran slot blots with total nucleic acid extracts of a panel of 72 strains of 14 different bacteria that the signal strengths were comparable when hybridized with $^{32}p$ labeled UP9A.

TABLE 4

A Comparison of Bacterial Cell Numbers Determined By Micro-Cultural and Probe Analysis.

| Sample | Total Bacterial Count | |
|---|---|---|
| | Culture | Probe |
| 1. | $1 \times 10^7$ | $6 \times 10^6$ |
| 2. | $4 \times 10^7$ | $2 \times 10^7$ |
| 3. | $5 \times 10^7$ | $5 \times 10^7$ |
| 4. | $6 \times 10^6$ | $3 \times 10^6$ |
| 5. | $8 \times 10^6$ | $6 \times 10^7$ |
| 6. | $2 \times 10^7$ | $6 \times 10^7$ |
| 7. | $5 \times 10^6$ | $3 \times 10^7$ |
| 8. | $1 \times 10^7$ | $6 \times 10^7$ |
| 9. | $4 \times 10^6$ | $6 \times 10^6$ |
| 10. | $9 \times 10^5$ | $3 \times 10^6$ |
| 11. | $1 \times 10^6$ | $3 \times 10^6$ |
| 12. | $3 \times 10^6$ | $1 \times 10^7$ |
| 13. | $5 \times 10^5$ | $2 \times 10^6$ |
| 14. | $1 \times 10^7$ | $6 \times 10^6$ |
| 15. | $1 \times 10^7$ | $6 \times 10^6$ |
| 16. | $1 \times 10^5$ | $1 \times 10^5$ |
| 17. | $8 \times 10^4$ | $1 \times 10^5$ |
| 18. | $2 \times 10^6$ | $2 \times 10^7$ |
| 19. | $1 \times 10^7$ | $6 \times 10^6$ |
| 20. | $5 \times 10^6$ | $2 \times 10^7$ |

Since the microbiological cell count represent only live bacteria it is expected that probe cell count will generally be higher, since it detects the presence of total nucleic acid isolated from both viable and non-viable bacteria.

Procedure

Plaque samples were collected by curette and deposited into 2 ml of a buffer (0.115M NaCl, 0.2M Tris-HCl, pH 7.5, 0.01M EDTA, pH 7.5 and 0.01M EGTA). When done carefully, one can reproducibly remove up to 90% of the bacteria present in an oral tooth pocket using curettes. The remaining amount of each sample (after 1/20th was taken for microbiology culturing was stored at $-20°$ C. for several days. Upon thawing, the samples were treated with 1% W/V SDS and 1 mg/ml proteinase K. The total nucleic acid was extracted with two phenol-chloroform extractions and then precipitated with ethanol. The pellet was resuspended in TE (10 mM Tris, 1MM EDTA), heated for one minute at 95° C. in the presence of 10 mM Pipes, pH 7.6, and slotted onto a Nytran membrane filter. The nucleic acid was immobilized onto the Nytran filter by baking for 1 hour at 80° C. This filter was probed with kinased 32-P labeled universal primer oligonucleotide (UP9A) in a 30% formamide hybridization solution (30% formamide 0.6M NaCl, 90 mM Tris 10 mM EDTA 0.5% W/V SDS 5X Denhardt's 100 µg/ml hydrolyzed yeast-RNA) at 43° C. for 16 hours. The filter was washed in 0.09M NaCl, 9 mM Tris, 0.6 mM EDTA at 50° C. then exposed to x-ray film. The resulting autoradiograph was compared to a standard of cultured bacteria, prepared and treated in the same manner (see below).

Cultured Bacteria Standard

The total nucleic acid from a known number of actively growing cultured bacteria were extracted as above, then nucleic acid carefully extracted, serially diluted, slotted and subsequently probed with the same universal primer oligonucleotide. The resulting autoradiograph indicated the intensity of the signal for a known number of bacteria. This standard curve was then used to estimate the amount of total nucleic acid present in the unknown samples.

EXAMPLE 3

The UP9A Probe is a Universal Probe for Eubacteria Plastids

Tests were conducted against 78 different strains of bacteria including the following genera: Actinobacillus, Haemophilus, Bacteroides, Eikenella, Fusobacterium, Wolinella, Campylobacter, Escherichia, Peptostreptococcus, Streptococcus, Capnocytophaga, Selenomonas, Actinomyces and Fusobacterium. Nucleic acids from the different bacteria were extracted and slotted onto a Nytran filter. This filter was then probed with a kinased UP9A oligo in a 30% formamide, 0.6M NaCl hybridization solution at 43° C. for 16 hours. The filter was then washed in a 0.09M NaCl/0.1% SDS solution at 50° C. before exposure to X-ray film. The degree of hybridization was rated for all species tested, strong (3), medium (2), weak (1), none detected (0). UP9A gave strong hybridization results for all bacterial species tested.

UP9A is a universal probe for eubacteria and plastids. The probe hybridizes specifically with nucleic acids (especially rRNA) from these two groups. The probe hybridizes only weakly to archaebacteria and eukaryote nucleic acids.

EXAMPLE 4

Total Bacterinal Counts Using Sandwich Assays

To demonstrate that in the sandwich assay using UP9A as a capture oligonucleotide and terminal transferase polybiotinylated UP3A and UP7B as signal oligonucleotides, total bacterial cell numbers were determined first in mixed periodontal bacterial cell cultures and secondly in plaque samples. About 50 plaque samples were classified by a dental hygienist as severe, moderate and normal according to clinical parameters used in the dental field. The samples were analyzed in a sandwich assay using UP9A as a capture probe. In preliminary results, its was found that there was a positive trend between disease severity and total bacteria present. The total bacteria counts were not done on these samples and we cannot make an absolute conclusion at this time.

A mixture of the seven PD-bacteria was constructed in equal number ratios. It was determined that the cells were actively growing by gel electrophoresis, wherein all the PD bacteria cultures had strong ribosomal RNA bands. In a sandwich assay using UP9A capture oligonucleotides and polybiotinylated signal oligonucleotides indicated that each individual bacterium yielded about the same signal except for W.recta where it was slightly lower.

EXAMPLE 5

UP9A Exhibits Low Crossreactivity with Human Cells

UP9A is particularly specific for bacteria and exhibits low crossreactivity with nucleic acid of human origin. Four human tissue culture cell types (A549—lung carcinoma, HeLa and SiHa—both cervical carcinomas, and T2—lymphoma) were lysed in GM GnSCN. Fresh blood was lysed also lysed in GnSCN. $10^8$, $10^7$, $10^6$ and $10^5$ bacterial cell equivalents (bce) of human cells and PD bacterial cells (control), plus 5 and 25 $\mu$l of blood were set up in the 100 $\mu$l volume sandwich assay. It is assumed that human nucleic acid is a 1000 times more complex than bacterial nucleic acid.

Capture: UP9A filters
Signal: UP3 AM and UP7M
Hybridization time: 40 minutes

Only a faint signal was seen at $10^8$ bce of human cells. Blood filters faintly tan with 5 $\mu$l and darker with 25 $\mu$l, but with no apparent blue signal. Therefore, contribution of signal from human sources appears to be minimal and only when very large numbers of cells present.

The slight background seen with human nucleic acid at $1 \times 10^8$ bce or $1 \times 10^5$ human cells can be eliminated by changing the stringency. Moreover, it is also expected that fewer than $1 \times 10^5$ human cells will be present in plaque samples.

*E. coli* bacteria and SiHa cells were used as positive and negative controls in the assays respectively. It has previously been shown on slot blots that UP9A showed no crossreactivity with nucleic acids from SiHa cells. In the sandwich assay format with vigorous shaking used in this study, however, some faint crossreactivity or non-specific interaction signal was seen with SiHa cells numbers as shown below:

| Cell number cells | Assay time min |
| --- | --- |
| $1 \times 10^5$ | 30 |
| $1 \times 10^4$ | 60 |

This low degree of crossreactivity does not interfere with the usefulness of UP9A as a universal probe for bacteria.

EXAMPLE 6

Specific Detection of Bg Bacterium in Pyrrolidone-Based Hybridization Media

A hybridization media composed of 20% N-cyclohexyl-2-pyrrolidone, and 20% N-Hydroxymethyl-2-pyrrolidone, 50 mM Tris, pH 7.6, 25 mM EDTA, and 2% SDS was used to lyse $1 \times 10^8$ cells of Aa, Bi, Ec, Wr, Fn, or Bg in 100 microliter volumes at 19° C. Biotinylated 24-mer oligonucleotide probes complementary to conserved regions of bacterial 16s rRNA (target probes) were added to a final concentration of 100 nanograms per ml. This solution was then incubated with nytran discs which had covalently immobilized 1 microgram of Bg specific oligonucleotide probe (capture probe, see Table 6) for 1 hour at ambient temperature. The solid supports were then washed with SDS/FW at ambient temperature and then incubated with 10 ng/ml of Strepavidin/Horseradish peroxidase (SA/HRP) conjugate in SDS/FW for 30 minutes at ambient temperature. The solid supports were then washed with SDS/FW, FW, and then the presence of peroxidase was determined by incubating the filter in 0.1M citrate-phosphate buffer, pH 5.5 containing 90 $\mu$M 3-methyl-2-benzothiazolinone hydrazone, 6 mM 4-methoxynaphthol and 4 mM hydrogen peroxide to form an insoluble product. The results indicated that only the Bg bacterium was detected in the colorimetric sandwich assay. The pyrrolidone hybridization media therefore promoted effective lysis and specific nucleic acid base pairing of the target nucleic acid. By comparison with serial dilution direct correlation was recorded between cell members and color density.

EXAMPLE 7

One Step Assay to Detect Specific Nucleic Acid Sequences of Bacterial Pathogens A pre-prepared lysis solution composed of 20% N-cyclohexyl-2-pyrrolidone, 20% N-hydroxymethyl-2-pyrrolidone, 10% N-dodecyl-2-pyrrolidone 50 mM Tris pH 7.6, 25 mM EDTA and 2% SDS(PLS) and containing 1 to 5 mg of 5 micron beads (silica, (Spherisorb) from Phase Sap, Deeside Ind., Queensferry, Clwyd, U.K.) onto which 1 to 2 micrograms of *Bacteroides gingivalis* (Bg) specific oligonucleotide probe (see Table 6) has been covalently immobilized, and which also contained $1 \times 10^6$ cpm of $^{32}$p oligonucleotide probe (specific activity of $1 \times 10^7$ cpm per microgram) complementary to Bg specific regions of the 16s rTNA was used to lyse $1 \times 10^6$ cells of Aa, Bi, Ec, Wr, Fn, and Bg in 100 microliter volumes at 19° C. The solution was then incubated for 30 minutes at room temperature. The solid supports were then washed with SDS/FW at ambient temperature to remove un-hybridized material and radioactive probes. The solid supports were then monitored for radioactivity by scintillation counting. The results indicated that only Bg cells were detected when using Bg specific oligonucleotide signal probes and not when using specific label ed probes for Aa, Bi, Ek, Fn or Wr. Thus, in 30 minutes $1 \times 10^6$ Bg cells were detected in a simple one step hybridization assay. By comparison with serial dilutions, direct correlation can be recorded between cell members and radioactive intensity.

EXAMPLE 8

Assay to Detect Specific Nucleic Acid Sequences of Pathogenic Bacteria in a Proteinase K/SDS/quanidine Thiocyanate Lysis/Hybridization Solution A pre-prepared solution composed of 0.2 mg/ml Proteinase K, 0.2% SDS in anaerobic growth media (brain heart infusion 30 g/l, soluble starch 10 g/l, gelatin 1 g/l in 10 mM pipes buffer pH8), are added to $1 \times 10^8$ cells of Aa, Bi, Bg, Ec, Wr, Fn cultured bacteria respectively and left at room temperature for 3 minutes. An equal volume of 6M guanidine thiocyanate lysis solution containing 100 ng/ml of biotinylated 24-mer oligonucleotide probes complementary to the conserved regions of the bacterial 16S rRNA is added (UP9A). This solution is then incubated with nytran discs which has covalently immobilized 1 microgram of Aa, Bg, Bi, Ec, Wr, Fn specific oligonucleotide probes (capture probe) respectively for 20 minutes at ambient temperature. The solid supports were then washed with SDS/FW at ambient temperature and then incubated with 10 ng/ml of Strepavidin/Horseradish peroxidase (SA/HRP ) conjugate in SDS/FW for 5 to 10 minutes at ambient temperature. The solid supports were then washed with SDS/FW, FW, and then the presence of peroxidase was determined by incubating the filter with substrates that formed an insoluble product as described in Example 1. The results will indicate that the bacteria are detected in the colorimetric sandwich assay when their specific capture probe was used and that there is a direct relationship between color intensity and cell numbers.

The above procedure was compared to procedures identical to it except that a) the bacteria was lysed and hybridized directly in the 3M GuCLS at ambient temperature b) a procedure where the bacteria was lysed in 3M Guanidine thiocyanate (GUSCN), 50 mM Tris-HCl (pH 7.6) 2% (w/v) Sarkosyl®, 0.12M β-mercaptoethanol and heated to 65° C. for 10 minutes before hybridization was performed at room temperature and c) a procedure where the bacteria was lysed directly in PLS. The following relative sensitivities were observed for the 4 procedures as shown in Table 5:

TABLE 5

Comparison of the Sensitivities of the Different Lysis/Hybridization Procedures.

| Lysis/Hybridization | Relative Sensitivity |
|---|---|
| GuCLS ambient temperature (ATemp) | 1 |
| Heated GuCLS | 10-25 |
| Proteinase K/SDS/GuCSN ATemp | 10-25 |
| Pyrrolidone lysis solution (PLS) Atemp | 5-10 |

EXAMPLE 9

Kit for Diagnosing Periodontal Disease by Measuring Total Bacterial Load

The following components would comprise a kit useful for diagnosing periodontal disease by estimating total bacterial load in tooth pockets.

Product Insert. The Product Insert will contain complete written instructions for patient sampling and evaluation. The instructions will follow the procedures of Example 4.

Data Card. A Data Card will be included for the recording of minimal baseline data for each patient, such as patient identification, site of collection, and test results.

Curettes. Curettes for sampling by scraping.

Endodontic Points. Endodontic points (paper points) for collection of each sample to be tested are also included. After cleansing the supragingival surfaces by wiping with gauze, the point will be used to rub the bacteria from the subgingival surface of the tooth to be sampled and to collect bacteria by absorption of saliva, gingival fluid, and gingival plaque.

Lysing Reagent. Each point or curette with the collected sample will be placed immediately into a numbered tube of Lysing Reagent which will lyse the bacteria and release the bacterial nucleic acids.

Probe/Enzyme Reagent. A standard aliquot of probe labeled by a ligand with or directly conjugated to an Enzyme Reagent is added to each tube of Lysing Reagent to initiate the hybridization reaction between the bacterial nucleic acid targets and the signal oligonucleo-

TABLE 6

Probes Derived from Hypervariable and Conserved Regions of the 16S and 23S Ribosomal RNA which are Free of Secondary and Tertiary Interactions.

| Oligonucleotide probe | | E. coli base position |
|---|---|---|
| *16S rRNA Hypervariable Regions* | | |
| Aa-4B | 5'ACCCATCTCTGAGTTCTTCTTCGG3' | 990-1030 |
| Aa-10B | 5'TGGCATGCTATTAACACACCAACC3' | 445-475 |
| Bg-6B | 5'CCTTAGGACAGTCTTCCTTCACGC3' | 395-430 |
| Bg-8B | 5'GGTTTTCACCATCAGTCATCTACA3' | 990-1030 |
| Bg-5B | 5'CCGATGCTTATTCTTACGGTACAT3' | 475-505 |
| Bi-3B | 5'CACGTGCCCCACTTTACTCCCCAA3' | 445-475 |
| Bi-5B | 5'GAGTCAACATCTCTGTATCCTGCG3' | 990-1030 |
| 2Bi-2B | 5'CGTGCGCCAATTTATTCCCACATA3' | 445-475 |
| Eik-4B | 5'GTACGCTACTAAGCAATCAAGTTG3' | 828-865 |
| Eik-2B | 5'GCACTTCCCTTTTCTTCCCTAACA3' | 445-475 |
| Eik-5B | 5'CTTCCGTCTCTGGAAGGTTCCGTAC3' | 990-1030 |
| Fn-2B | 5'GTTGGTACCGTCATTTTTTTCTTC3' | 445-475 |
| Fn-4B | 5'TCAGACTCTCGGTCCATTGTCCAA3' | 445-475 |
| Fn-6B | 5'AAACATCTCTGTCTCATTCCTAAG3' | 990-1030 |
| Wr-1B | 5'GTACCGTCATAATTCTTTCCCAAG3' | 445-475 |
| Wr-6B | 5'CTTGGGTACCGTCATAATTCTTTCC3' | 445-475 |
| *23S rRNA Hypervariable Regions* | | |
| Bg23-2 | 5'GTACGGGTAACACAGAAATATGCT3' | 1570-1620 |
| Bg23-4 | 5'GACTATATACCTCAAATTGCTTTT3' | 1800-1830 |
| Bg23-6 | 5'CCTACACATCTGATGCCAAATACA3' | 2085-2120 |
| *16S rRNA Conserved Regions* | | |
| UP2D | 5'CCCGTCWATTCMTTTGAGTTTT3' | 906-927 |
| UP3A | 5'TGACGGGCGGTGTGTACAA3' | 1390-1408 |
| UP7B | 5'GTATTACCGCGGCTGCTG3' | 519-536 |
| UP9A | 5'CTGCTGCCTCCCGTAGGAGT3' | 338-357 |
| UP20B | 5'GACTACYMGGGTATCTAATCC3' | 785-805 |
| UP21A | 5'TTAAACCACATGYTCCWCCGCTTG3' | 936-959 |
| *23S rRNA Conserved Regions* | | |
| UP12B | 5'TYGATTGGCMTTTCACCCC3' | 775-793 |
| 23UPB | 5'CCGGTCCTCTCGTACTA3' | 2653-2669 |
| 23UPJ | 5'TTCGCTCGCCGCTACT3' | 241-256 |
| 23UPM | 5'GTTATAGTTACGGCCGCCGTTTAC3' | 1897-1920 | tide probes derived from conserved regions of the ribosomal RNA sequences.

Dipstick Device. An individual Dipstick Device containing site(s) with bacteria-specific DNA probes covalently immobilized to the solid support and having space for marking and identifying each site tooth sampled, is inserted immediately into each tube containing the hybridization mixture and incubated at room temperature.

Wash Reagent. Each Dipstick Device is removed from the hybridization mixture and washed with the Wash Reagent, using the container provided.

Enzyme Substrate Reagent. The Dipstick Devices are placed collectively into the Enzyme Substrate Reagent container and developed for several minutes to 1 hour at room temperature. Each Dipstick Device is washed again with the Wash Reagent to remove excess background color.

Reference Card. Color development is visualized and compared with a Reference Card, indicating the quantity of bacteria by comparisons with known standards.

We claim:

1. A method of measuring the quantity of bacteria in a biological sample said method consisting essentially of the following steps:
   (A) lysing the bacteria in the biological sample under conditions that release target ribosomal RNA (rRNA), wherein the target rRNA has minimal disturbance of secondary structure and is non-denatured;
   (B) contacting the target rRNA with an immobilized oligonucleotide capture probe wherein;
      (i) hybridization conditions are nondenaturing for the target rRNA; and
      (ii) the capture probe consists of a sequence selected from the group consisting of 5'X-CTGCTGCCTCCCGTAGGAGT-X3', 5'X-GTATTACCGCGGCTGCTG-X3' and concatemers of said sequences, wherein each X is the same or different as the other X and is from 0 to 10 nucleic acid bases; and
   (C) determining total bacteria in the sample.

2. The method of claim 1 wherein the lysing step is performed with a lysis solution selected from the group consisting of an enzyme/chaotrope solution, a chaotrope/detergent solution, an enzyme/formamide solution and an enzyme/detergent solution.

3. The method of claim 2 wherein the lysing step is performed at room temperature with a lysis solution containing about 2M to about 4M guanidinium thiocyanate.

4. The method of claim 2 wherein the lysing step is performed at room temperature with a lysis solution containing a protease and about 2M to about 4M guanidinium thiocyanate.

5. The method of claim 1 wherein the oligonucleotide signal probe is selected from the group consisting of 5'CTGCTGCCTCCCGTAGGAGT3 ', 5'GTATTACCGCGGCTGCTG3 ' and 5'TGACGGGCGGTGTGTACAA3'.

6. The method of claim 1 wherein the oligonucleotide capture probe is 5'CTGCTGCCTCCCGTAGGAGT3' and the oligonucleotide signal probe is 5'GTATTACCGCGGCTGCTG3' or 5'TGACGGGCGGTGTGTACAA3'.

7. The method of claim 1 wherein the determining step is performed by comparing intensity of signal associated with the biological sample to intensity of signal associated with a known quantity of bacteria.

8. A method for detecting bacteria in a biological sample said method consisting essentially of the following steps:
   (A) combining the biological sample with a lysis solution capable of releasing bacterial ribosomal RNA (rRNA) in a non-denatured form and having minimal disturbance of secondary structure;
   (B) contacting the rRNA with an immobilized oligonucleotide capture probe and with an oligonucleotide signal probe having a detectable label attached thereto, and wherein
      (i) the capture probe and signal probe are added to the rRNA either simultaneously or sequentially;
      (ii) hybridization conditions are non-denaturing for the rRNA;
      (iii) the capture probe is selected from the group consisting of 5'CTGCTGCCTCCCGTAGGAGT3', and 5'GTATTACCGCGGCTGCTG3; and
      (iv) signal probe sequence is nonidentical to capture probe sequence; and
   (C) assaying for the presence of detectable label to detect bacteria in the sample.

9. The method of claim 8 wherein the lysis solution is selected from the group consisting of an enzyme/chaotrope solution, a chaotrope/detergent solution, an enzyme/formamide solution and an enzyme/detergent solution.

10. The method of claim 9 wherein the combining step is performed at room temperature and the lysis solution contains about 2M to about 4M guanidinium thiocyanate.

11. The method of claim 9 wherein the combining step is performed at room temperature and the lysis solution contains a protease and about 2M to about 4M guanidinium thiocyanate.

12. The method of claim 8 wherein the oligonucleotide signal probe is selected from the group consisting of 5'CTGCTGCCTCCCGTAGGAGT3', 5'GTATTACCGCGGCTGCTG3' and 5'TGACGGGCGGTGTGTACAA3'.

13. The method of claim 8 wherein the oligonucleotide capture probe is 5'CTGCTGCCTCCCGTAGGAGT3' and the oligonucleotide signal probe is 5'GTATTACCGCGGCTGCTG3' or 5'TGACGGGCGGTGTGTACAA3'.

14. A method for quantitating bacterial load in a sample using a nucleic hybridization assay said method consisting essentially of the following steps:
   (A) combining a biological sample with a lysis solution capable of releasing bacterial ribosomal RNA (rRNA) in a non-denatured form and having minimal disturbance of secondary structure;
   (B) contacting the bacterial rRNA with an immobilized oligonucleotide capture probe wherein
      (i) the hybridization conditions are non-denaturing for the bacterial rRNA; and
      (ii) the capture probe consists of a sequence selected from the group consisting of 5'X-CTGCTGCCTCCCGTAGGAG-X3', 5'X-GTATTACCGCGGCTGCTG-X3' and concatemers of said sequences, wherein each X is the same or different as the other X and is from 0 to 10 nucleic acid bases; and
   (C) comparing the quantity of rRNA captured with a standard amount of nucleic acid or with a signal representing a standard amount of nucleic acid to quantitate the bacterial load in the sample.

15. The method of claim 14 wherein the combining step is performed at room temperature with a lysis solution selected from the group consisting of a chaotrope solution, an enzyme/chaotrope solution, a chaotrope/detergent solution, an enzyme/formamide solution and an enzyme/detergent solution.

16. The method of claim 15 wherein the combining step is performed at room temperature with a lysis solution containing about 2M to about 4M guanidinium thiocyanate.

17. The method of claim 15 wherein the combining step is performed at room temperature with a lysis solution containing a protease and about 2M to about 4M guanidinium thiocyanate.

18. The method of claim 14 wherein the oligonucleotide signal probe is selected from the group consisting of 5'CTGCTGCCTCCCGTAGGAGT3', 5'GTATTACCGCGGCTGCTG3' and 5'TGACGGGCGGTGTGTACAA3'.

19. The method of claim 14 wherein the oligonucleotide capture probe is 5'CTGCTGCCTCCCGTAGGAGT3' and the oligonucleotide signal probe is 5'GTATTACCGCGGCTGCTG3' or 5'TGACGGGCGGTGTGTACAA3'.

* * * * *